United States Patent
An et al.

(10) Patent No.: US 12,253,486 B2
(45) Date of Patent: Mar. 18, 2025

(54) SELF-HEATING GAS SENSOR, GAS-SENSITIVE MATERIAL, PREPARATION METHOD FOR SAME, AND APPLICATIONS THEREOF

(71) Applicants: CHINA PETROLEUM & CHEMICAL CORPORATION, Beijing (CN); SINOPEC RESEARCH INSTITUTE OF SAFETY ENGINEERING CO., LTD., Shandong (CN)

(72) Inventors: Fei An, Shandong (CN); Bing Sun, Shandong (CN); Na Li, Shandong (CN); Lin Wang, Shandong (CN); Ning Shi, Shandong (CN); Wei Xu, Shandong (CN); Shucai Zhang, Shandong (CN); Haozhi Wang, Shandong (CN); Shiqiang Wang, Shandong (CN); Junjie Feng, Shandong (CN); Chenyang Zhao, Shandong (CN)

(73) Assignees: CHINA PETROLEUM & CHEMICAL CORPORATION, Beijing (CN); SINOPEC RESEARCH INSTITUTE OF SAFETY ENGINEERING CO., LTD., Shandong (CN)

( * ) Notice: Subject to any disclaimer, the term of this patent is extended or adjusted under 35 U.S.C. 154(b) by 255 days.

(21) Appl. No.: 17/906,232

(22) PCT Filed: Jan. 26, 2021

(86) PCT No.: PCT/CN2021/073734
§ 371 (c)(1),
(2) Date: Sep. 13, 2022

(87) PCT Pub. No.: WO2021/203804
PCT Pub. Date: Oct. 14, 2021

(65) Prior Publication Data
US 2023/0124633 A1    Apr. 20, 2023

(30) Foreign Application Priority Data

Apr. 10, 2020   (CN) .......................... 202010280974.5

(51) Int. Cl.
*G01N 27/12*    (2006.01)
*G01N 33/00*    (2006.01)
(Continued)

(52) U.S. Cl.
CPC ......... *G01N 27/127* (2013.01); *G01N 27/128* (2013.01); *G01N 33/0027* (2013.01); *B82Y 15/00* (2013.01); *B82Y 40/00* (2013.01)

(58) Field of Classification Search
CPC ............... G01N 27/127; G01N 27/128; G01N 33/0027; G01N 27/125; B82Y 15/00;
(Continued)

(56) References Cited

U.S. PATENT DOCUMENTS

| 5,627,305 A | 5/1997 | Yun et al. |
| 2012/0161796 A1 | 6/2012 | Smith et al. |

(Continued)

FOREIGN PATENT DOCUMENTS

| CN | 1141433 A | 1/1997 |
| CN | 101439855 A | 5/2009 |

(Continued)

OTHER PUBLICATIONS

Chang, Xueting et al.; "Graphene-tungsten oxide nanocomposites with highly enhanced gas-sensing performance"; Journal of alloy and Compounds, vol. 705; Year: 2007; pp. 1-31.
(Continued)

*Primary Examiner* — Robert R Raevis
(74) *Attorney, Agent, or Firm* — NKL Law; Allen Xue

(57) ABSTRACT

A gas-sensitive material, a preparation method therefore and an application thereof, and a gas sensor using the gas-sensitive material are provided. The gas-sensitive material is a carbon material-metal oxide composite nanomaterial formed by compounding a carbon material and metal oxides.

(Continued)

The content of the carbon material is 0.5~20 wt. % and the content of the metal oxides is 80~99.5 wt. %; the metal oxides contain tungsten oxide and one or more selected from tin oxide, iron oxide, titanium oxide, copper oxide, molybdenum oxide, and zinc oxide; the metal oxides are formed on the carbon material in the form of nanowires, and the nanowires are tungsten oxide-doped nanowires. The gas-sensitive material has reduced resistance, is capable of responding to various gases at a reduced working temperature.

20 Claims, 7 Drawing Sheets

(51) Int. Cl.
 *B82Y 15/00* (2011.01)
 *B82Y 40/00* (2011.01)
(58) Field of Classification Search
 CPC ........ B82Y 40/00; B82Y 30/00; C01G 41/00;
  C01G 49/0018; C01G 3/02; C01G 9/02;
  C01G 15/00; C01G 19/02; C01G 39/02;
  C01G 41/02; C01G 49/06; C01P 2002/77;
  C01P 2004/03; C01P 2004/04; C01P
  2004/16; C01P 2004/20; C01P 2004/61;
  C01P 2002/54; C01P 2004/62; C01P
  2006/40; C01P 2004/80; C01B 32/174;
  C01B 32/194; C01B 32/156; C01B
  32/184; C01B 32/168
 USPC ......... 73/23.3, 31.02, 31.05, 31.06; 324/691,
  324/693, 713–715, 717, 722; 422/83, 88,
  422/90, 94, 98; 338/13, 14, 34
 See application file for complete search history.

(56) References Cited

U.S. PATENT DOCUMENTS

| | | |
|---|---|---|
| 2016/0218353 A1 | 7/2016 | Kim et al. |
| 2018/0215628 A1 | 8/2018 | Lee et al. |

FOREIGN PATENT DOCUMENTS

| | | |
|---|---|---|
| CN | 101824603 A | 9/2010 |
| CN | 101913597 A | 12/2010 |
| CN | 102502842 A | 6/2012 |
| CN | 102531063 A | 7/2012 |
| CN | 104807860 A | 7/2015 |
| CN | 105606659 A | 5/2016 |
| CN | 106596652 A | 4/2017 |
| CN | 106770476 A | 5/2017 |
| CN | 107298464 A | 10/2017 |
| CN | 108398408 A | 8/2018 |
| CN | 109632895 A | 4/2019 |
| CN | 109839408 A | 6/2019 |
| CN | 110127671 A | 8/2019 |
| CN | 110161091 A | 8/2019 |
| CN | 110498405 A | 11/2019 |
| CN | 110759376 A | 2/2020 |
| GB | 2464516 A | 4/2010 |
| JP | H08261970 A | 10/1996 |
| WO | 2018216952 A1 | 11/2018 |

OTHER PUBLICATIONS

Wondimu, Tadele Hunde et al.; "Highly efficient and durable phosphine reduced iron-doped tungsten oxide/ reduced graphene oxide nanocomposites for the hydrogen evolution reaction"; International Journal of Hydrogen Energy, vol. 43, Issue 13; Year 2018; pp. 6481-6490.

Piloto, Carlo et al.; "Sensing performance of reduced graphene oxide-Fe doped WO3 hybrids to NO2 and humidity at room temperature"; Applied surface Science, vol. 434; Mar. 15, 2018; pp. 1-33.

Vallejos, Stella et al.; "Nanoscale Heterostructures Based on Fe2O3@WO3-x Nanoneedles and Their Direct Integration into Flexible Transducing Platforms for Toluene Sensing"; ACS Applied Materials & Interfaces, vol. 7, No. 33; Year: 2015; pp. 18638-18649.

Yin, Li et al.; "Construction and Gas Sensing Properties of Tungsten Oxide Nanosheets and Graphene-Based Hierarchical Composite Nanomaterials"; Zhengzhou University doctoral dissertation; May 2015: pp. 19, 103 and 114.

SELF-HEATING GAS SENSOR, GAS-SENSITIVE MATERIAL, PREPARATION METHOD FOR SAME, AND APPLICATIONS THEREOF

CROSS-REFERENCE TO RELATED APPLICATIONS

This application is a U.S. national stage entry of PCT International Application No. PCT/CN2021/073734, filed on Jan. 26, 2021, which claims the priority of Chinese Patent Application No. 202010280974.5, filed on Apr. 10, 2020, with China National Intellectual Property Administration, titled "SELF-HEATING GAS SENSOR, GAS-SENSITIVE MATERIAL, PREPARATION METHOD FOR SAME, AND APPLICATIONS THEREOF", the content of which is incorporated herein by reference in its entirety.

FIELD

The present disclosure relates to the field of materials, in particular to a gas-sensitive material, a preparation method therefor and a use thereof, and a self-heating gas sensor based on Joule principle, which uses the gas-sensitive material.

BACKGROUND

In recent years, the environmental pollution problem has become more and more prominent. Therefore, it is one of the top priorities to solve the environmental pollution problem. As one of the major sources of environmental pollution, toxic and harmful gases widely exist in the production, transportation and storage processes of petroleum and chemical enterprises, and always threaten the health and safety of the workers. It is one of urgent tasks to quickly and accurately detect the concentrations of toxic and harmful gases and ensure personal safety in industry.

It is one of the effective approaches to solve the problem by preparing gas sensors based on metal oxide nanomaterials. Metal oxide nanomaterials not only reduce the consumption of sensing materials and greatly reduce the cost, but also improve the gas sensing performance of the sensors owing to the small size effect of the nanomaterials. However, gas sensors based on metal oxide nanomaterials have to be heated up to 200-400° C. to work normally, in view of the disadvantage of extremely low electric conductivity of metal oxides at room temperature. According to statistics, almost 60% of the energy of a sensor is used to heat the sensing material. That fact not only causes increased energy consumption and is adverse to sensor miniaturization and long-time use, but also brings potential safety hazards. Therefore, in recent years, how to prepare sensors with low energy consumption and excellent gas sensing performance has become one of the research hotspots in the field of gas sensors.

At present, there are two commonly used methods for reducing the energy consumption of gas sensors: 1. Preparing novel nanometer gas-sensitive materials. At present, carbon materials, such as graphene, carbon nanotubes and fullerene, etc., are the research topics. These materials have very high electric conductivity and great specific surface area, and their selectivity to different gases can be changed by surface modification. Therefore, these materials can respond to target gases at room temperature without heating, thus the energy consumption is reduced. 2. Self-heating under a Joule heat principle. Joule heat refers to the heat generated when current flows through a conductor. Therefore, by regulating and controlling the resistance of a gas-sensitive material and the applied measuring voltage, the gas-sensitive material can be heated by using the current provided by the measuring circuit. Moreover, since the heating is directly achieved by the gas-sensitive material without any intermediate heat conduction, the heat dissipation can be greatly reduced. In addition, the energy consumption is further reduced because the external heating circuit is removed. However, both of the methods have their respective disadvantages at present. 1. Although graphene, carbon nanotubes and other carbon materials can respond to gases at room temperature, their response recovery rate is very low and can't meet the requirement in actual life, because the gas adsorption/desorption process at room temperature is very slow. 2. At present, the gas sensors that utilize the Joule heat principle for self-healing mainly utilize a single or oriented metal or metal oxide nanowire or nanobelt. These sensors are prepared with a complex method and expensive instruments. Moreover, since the gas-sensitive materials have high resistance, a high voltage has to be applied to heat up the gas-sensitive materials to an ideal temperature. Consequently, the size of the battery is increased, adverse to the miniaturization and portability of the sensors.

SUMMARY

To solve the problems existing in the prior art, the present disclosure provides a gas-sensitive material, a preparation method therefor and a use thereof, and a self-heating gas sensor based on Joule principle, which uses the gas-sensitive material. The gas-sensitive material provided by the present disclosure has reduced resistance, is capable of responding to various gases at a reduced working temperature, also obviates the need for external heating, implements self-heating simply by Joule heating of a measuring circuit, and has reduced power consumption and increased sensitivity.

In order to attain the above object, in a first aspect, the present disclosure provides a gas-sensitive material for a self-heating gas sensor based on Joule principle, wherein the gas-sensitive material is a carbon material-metal oxide composite nanomaterial formed by compounding a carbon material and metal oxides, the content of the carbon material is 0.5~20 wt. % and the content of the metal oxide is 80~99.5 wt. % in the carbon material-metal oxide composite nanomaterial; the metal oxides contain tungsten oxide and one or more selected from tin oxide, iron oxide, titanium oxide, copper oxide, molybdenum oxide and zinc oxide, wherein the metal oxides are formed on the carbon material in the form of nanowires, and the nanowires are tungsten oxide-doped nanowires.

Preferably, the diameter of the nanowires is 10~100 nm, and the length of the nanowires is 500~10,000 nm.

Preferably, the metal oxides contain $WO_3$ and one or more selected from $SnO_2$, $Fe_2O_3$, $TiO_2$, CuO, $MoO_3$ and ZnO; more preferably, the metal oxides contain $WO_3$ and one or more selected from $SnO_2$, $Fe_2O_3$, $TiO_2$, CuO and $MoO_3$.

Preferably, based on the total weight of the metal oxides, the content of $WO_3$ preferably is 60~99.5 wt. %.

Preferably, the nanowires are tungsten trioxide-doped nanowires.

Preferably, the content of the carbon material is 0.5~15 wt. % and the content of the metal oxides is 85~99.5 wt. % in the carbon material-metal oxide composite nanomaterial.

Preferably, the carbon material is one or more of graphene, carbon nanotube, fullerene and carbon black.

According to a second aspect of the present disclosure, the present disclosure provides a method for preparing a gas-sensitive material, comprising the steps of carrying out heat treatment on a carbon material, and metal oxides and/or metal oxide precursors under microwaves in the presence of an alcohol solvent, and then carrying out solid-liquid separation, to obtain a carbon material-metal oxide composite nanomaterial, wherein the metal oxides contain tungsten oxide and one or more selected from tin oxide, iron oxide, titanium oxide, copper oxide, molybdenum oxide and zinc oxide; the metal oxide precursors are alcohol-soluble tungsten salt and one or more selected from alcohol-soluble tin salt, alcohol-soluble iron salt, alcohol-soluble titanium salt, alcohol-soluble copper salt, alcohol-soluble molybdenum salt and alcohol-soluble zinc salt.

Preferably, based on the total weight of the carbon material and the metal oxides, the amount of the carbon material is 0.5~20 wt. %, and the amount of the metal oxides is 80~99.5 wt. %; based on the total weight of the carbon material and the metal oxide precursors measured in the metal oxides, the amount of the carbon material is 0.5~20 wt. %, and the amount of the metal oxide precursors measured in the metal oxides is 80~99.5 wt. %.

Preferably, the carbon material is one or more of graphene, carbon nanotube, fullerene and carbon black.

Preferably, the metal oxides contain $WO_3$ and one or more selected from $SnO_2$, $Fe_2O_3$, $TiO_2$, $CuO$, $MoO_3$ and $ZnO$; more preferably, the metal oxides contain $WO_3$ and one or more selected from $SnO_2$, $Fe_2O_3$, $TiO_2$, $CuO$ and $MoO_3$.

Preferably, the metal oxide precursors are tungsten chloride and one or more selected from tin chloride, iron chloride, titanium chloride, copper chloride, molybdenum chloride and zinc chloride; more preferably, the metal oxide precursors are tungsten chloride and at least one selected from tin chloride, iron chloride, titanium chloride, copper chloride and molybdenum chloride.

Preferably, based on the total weight of the metal oxides, the content of the tungsten oxide is 60~99.5 wt. %.

Preferably, measured in the metal oxides, the amount of the alcohol-soluble tungsten salt in the metal oxide precursors is 60~99.5 wt. %.

Preferably, the alcohol solvent is ethanol.

Preferably, in relation to the total weight of the carbon material, the metal oxides and the metal oxide precursors, which is measured as 100 pbw, the amount of the solvent is 500~100,000 pbw.

Preferably, the conditions of the heat treatment include: microwave power: 200~1,800 W; heat treatment temperature: 160~220° C.; and heat treatment time: 10~240 min.

Preferably, the method further comprises a step of drying the carbon material-metal oxide composite nanomaterial obtained through separation.

Preferably, the method further comprises a step of reducing the carbon material-metal oxide composite nanomaterial with a reducing agent.

Preferably, a mass ratio of the carbon material-metal oxide composite nanomaterial measured in carbon element to the reductant is 1:(0.1~20).

Preferably, the reductant is one or more of sodium borohydride, lithium aluminum hydride, hydrogen iodide, hydrogen bromide, thiourea, ethanethiol, sodium persulfate, hydrazine hydrate, pyrrole, urea, ethanol, ascorbic acid, glucose, aluminum-hydrochloric acid, iron-hydrochloric acid, zinc-sodium hydroxide, zinc-ammonium hydroxide, glycine, lysine and green tea.

Preferably, the conditions of the reduction treatment include: reduction treatment temperature: 200~500° C.; and reduction treatment time: 0.1~12 h.

According to a third aspect of the present disclosure, the present disclosure provides a self-heating gas sensor based on Joule principle, comprising a chip carrier and a gas-sensitive material supported on the chip carrier, wherein the gas-sensitive material is the gas-sensitive material for a self-heating gas sensor based on Joule principle as described in the present disclosure.

Preferably, the gas-sensitive material is supported on the chip carrier by dripping, gas spraying, micro-spraying, deposition, or coating.

Preferably, the chip carrier is a ceramic tube and/or a MEMS chip.

According to a fourth aspect of the present disclosure, the present disclosure provides a use of the gas-sensitive material provided by the present disclosure in self-heating gas sensors based on Joule principle.

The gas-sensitive material provided by the present disclosure has reduced resistance, is capable of responding to various gases at a reduced working temperature (room temperature to 200° C.), also obviates the need for external heating, implements self-heating simply by Joule heating of a measuring circuit, and has reduced power consumption. In addition, the gas-sensitive material provided by the present disclosure requires a low measuring voltage, and can self-heat up to 200° C. temperature only at 1~20V. Thus, the gas-sensitive material provided by the present disclosure has higher sensitivity.

Furthermore, as shown in Test Example 2, the response recovery rate of the gas-sensitive material provided by the present disclosure is 20 s or shorter, i.e., the response recovery is very quick.

Furthermore, the gas-sensitive material provided by the present disclosure is a universal gas-sensitive material, which is capable of responding to various gases such as hydrogen sulfide, toluene, carbon monoxide, etc., and has an excellent response recovery rate especially for hydrogen sulfide.

Figure 1:
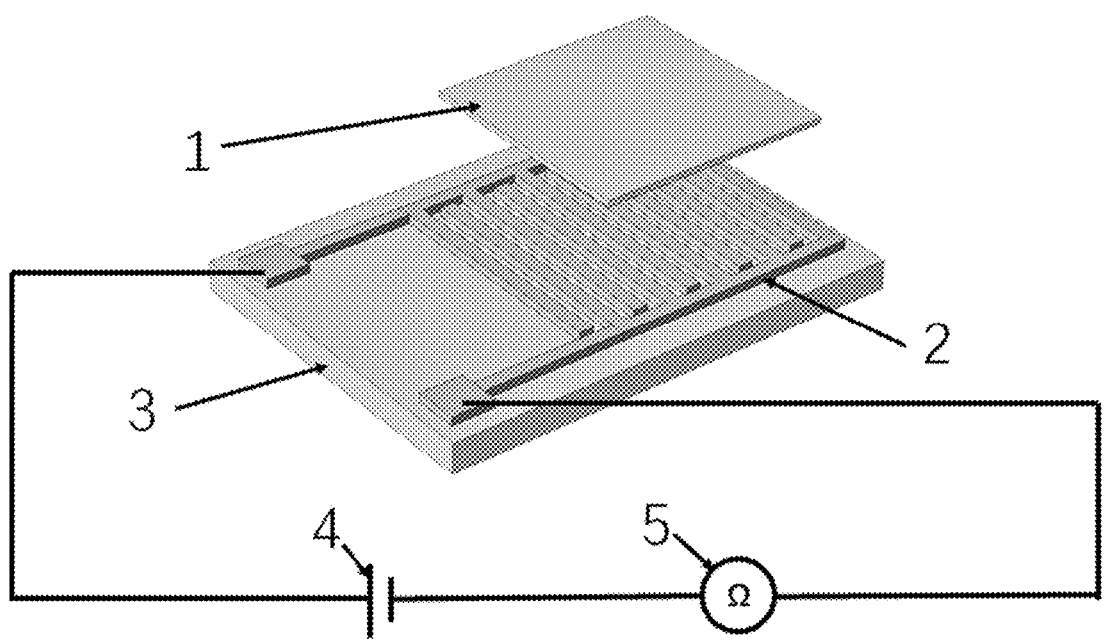
FIG. 1 is a schematic diagram of self-heating power test using a MEMS chip in Test Example 1.

| Reference Numbers | |
| --- | --- |
| 1: gas-sensitive material layer | 2: metal interdigital electrode |
| 3: silicon substrate | 4: power source meter |
| 5: ohmmeter | |

DETAILED DESCRIPTION

The end points and any value in the ranges disclosed in the present disclosure are not limited to the exact ranges or values; instead, those ranges or values shall be understood as encompassing values that are close to those ranges or values. For numeric ranges, combinations may be made between the end points of the ranges, between the end points of the ranges and the discrete point values, and between the discrete point values to obtain one or more new numeric ranges, which shall be deemed as having been disclosed specifically herein.

In a first aspect, the present disclosure provides a gas-sensitive material, wherein the gas-sensitive material is a carbon material-metal oxide composite nanomaterial formed by compounding a carbon material and metal oxides, the content of the carbon material is 0.5~20 wt. % and the content of the metal oxides is 80~99.5 wt. % in the carbon material-metal oxide composite nanomaterial; and the metal oxides contain tungsten oxide and one or more selected from tin oxide, iron oxide, titanium oxide, copper oxide, molybdenum oxide and zinc oxide, wherein the metal oxides are formed on the carbon material in the form of nanowires, and the nanowires are tungsten oxide-doped nanowires.

In the present disclosure, a "tungsten oxide-doped nanowire" refers to a structure in which one or more selected from tin oxide, iron oxide, titanium oxide, copper oxide, molybdenum oxide and zinc oxide are doped into tungsten oxide nanowires.

Examples of the tin oxide include: stannous oxide and tin dioxide, etc.; preferably tin dioxide.

Examples of the iron oxide include: ferric oxide, ferrous oxide, and ferroferric oxide, etc.; preferably ferric oxide.

Examples of the titanium oxide include: titanium dioxide and titanium suboxide, etc.; preferably titanium dioxide.

Examples of the copper oxide include: copper oxide and cuprous oxide, etc.; preferably copper oxide.

Examples of the molybdenum oxide include: molybdenum dioxide and molybdenum trioxide, etc.; preferably molybdenum trioxide.

Examples of the zinc oxide include: zinc oxide and zinc peroxide, etc.; preferably zinc oxide.

Through in-depth research, the inventor has found that the gas sensing performance can be significantly improved if the metal oxides are formed on the carbon material in the form of nanowires and the metal oxides have a structure of tungsten oxide-doped nanowires.

The diameter of the nanowires preferably is 10~100 nm, more preferably is 15~80 nm, further preferably is 15~50 nm, still further preferably is 18~40 nm. In addition, the length of the nanowires preferably is 500~10,000 nm, more preferably is 500~8,000 nm, further preferably is 550~7,000 nm, still further preferably is 550~5,000 nm.

According to the present disclosure, preferably, the metal oxides contain $WO_3$ and one or more selected from $SnO_2$, $Fe_2O_3$, $TiO_2$, CuO, $MoO_3$ and ZnO; more preferably, the metal oxides contain $WO_3$ and one or more selected from $SnO_2$, $Fe_2O_3$, $TiO_2$, CuO and $MoO_3$. The gas sensing performance can be further improved by means of the above combinations.

According to the present disclosure, to further improve the gas sensing performance, preferably, based on the total weight of the metal oxides, the content of the tungsten oxide preferably is 60~99.5 wt. %, more preferably is 70~99.5 wt. %.

The tungsten oxide preferably is tungsten trioxide.

According to the present disclosure, the gas-sensitive material can self-heat up to 200° C. solely at the measuring voltage. Therefore, the measuring voltage is low and the power consumption is low.

Specifically, when the gas-sensitive material is self-heated up from 25° C. to 200° C. at the measuring voltage, the consumed power is 9,000 µW or lower; preferably, when the gas-sensitive material self-heats up from 25° C. to 200° C. solely at the measuring voltage, the consumed power preferably is 8,800 W or lower, further preferably is 8,500 µW or lower, still further preferably is 8,000 µW or lower, still further preferably is 7,000 µW or lower, still further preferably is 6,000 µW or lower, still further preferably is 5,000 µW or lower, still further preferably is 4,000 µW or lower, and particularly preferably is 3,000 µW or lower. In addition, the consumed power preferably is 1,000 µW or higher, more preferably is 1,500 µW or higher, further preferably is 1,800 µW or higher, and still further preferably is 2,500 µW or higher.

According to the present disclosure, preferably, when the gas-sensitive material self-heats up from 25° C. to 100° C., the consumed power preferably is 2,000 µW or lower, further preferably is 1,800 µW or lower, still further preferably is 1,600 µW or lower, still further preferably is 1,400 µW or lower, still further preferably is 1,200 µW or lower, still further preferably is 1,000 µW or lower, and particularly preferably is 800 µW or lower. In addition, the consumed power preferably is 180 µW or higher, more preferably is 200 µW or higher, further preferably is 250 µW or higher, and still further preferably is 500 µW or higher.

According to the present disclosure, preferably, when the gas-sensitive material self-heats up from 25° C. to 50° C., the consumed power preferably is 120 µW or lower, further preferably is 110 µW or lower, still further preferably is 90 µW or lower, still further preferably is 85 µW or lower, and particularly preferably is 70 µW or lower. In addition, the consumed power preferably is 10 µW or higher, more preferably is 15 µW or higher, further preferably is 20 µW or higher, and still further preferably is 50 µW or higher.

According to the present disclosure, for example, the measuring voltage may be 1~20V, specifically 1V, 2V, 3V, 4V, 5V, 6V, 7V, 8V, 9V, 10V, 11V, 12V, 13V, 14V, 15V, 16V, 17V, 18V, 19V or 20V, etc.

According to the present disclosure, the content of the carbon material is 0.5~20 wt. %, and the content of the metal oxides is 80~99.5 wt. % in the carbon material-metal oxide composite nanomaterial; to reduce the working temperature, reduce the energy consumption, and improve the response rate and response recovery rate, preferably the content of the carbon material is 0.5~15 wt. % and the content of the metal oxides is 85~99.5 wt. % in the carbon material-metal oxide composite nanomaterial. In the present disclosure, when the content of the carbon material is higher than 20 wt. %, the gas-sensitive material has lowered resistance and lowered gas response rate and response recovery rate. When the content of the carbon material is lower than 0.5 wt. %, the gas-sensitive material has increased resistance, higher working temperature, increased heating voltage, and increased energy consumption.

According to the present disclosure, preferably, the resistance of the carbon material-metal oxide composite nanomaterial is 0.1~110 kΩ, more preferably is 1~100 kΩ.

According to the present disclosure, the carbon material may be any carbon material commonly used in the art; preferably, the carbon material is one or more of graphene, carbon nanotubes, fullerene and carbon black.

According to the present disclosure, the carbon material-metal oxide composite nanomaterial may be in a flaky shape, granular shape or linear shape, preferably is a flaky shape.

In the case that the carbon material-metal oxide composite nanomaterial is in a flaky shape, the thickness may be 0.5~100 nm, and the longest distance between two points may be 0.1~50 m; preferably, the thickness may be 1~50 nm, and the longest distance between two points may be 0.1~40 μm.

In the case that the carbon material-metal oxide composite nanomaterial is in a granular shape, the particle diameter may be 10~800 nm, preferably is 10~700 nm.

In the case that the carbon material-metal oxide composite nanomaterial is in a linear shape, the diameter may be 1~100 nm, and the length may be 0.1~200 μm; preferably, the diameter is 1~50 nm and the length is 0.1~100 μm.

According to a second aspect of the present disclosure, the present disclosure provides a method for preparing a gas-sensitive material, comprising the steps of carrying out heat treatment on a carbon material, and metal oxides and/or metal oxide precursors under microwaves in the presence of an alcohol solvent, and then carrying out solid-liquid separation, to obtain a carbon material-metal oxide composite nanomaterial, wherein the metal oxides contain tungsten oxide and one or more selected from tin oxide, iron oxide, titanium oxide, copper oxide, molybdenum oxide and zinc oxide; the metal oxide precursors are alcohol-soluble tungsten salt and one or more selected from alcohol-soluble tin salt, alcohol-soluble iron salt, alcohol-soluble titanium salt, alcohol-soluble copper salt, alcohol-soluble molybdenum salt and alcohol-soluble zinc salt.

According to the preparation method of the present disclosure, no surfactant is used in the heat treatment.

Since the carbon material, and the metal oxides or metal oxide precursors are heat-treated under microwaves, the raw material can be heated up to a target temperature by means of microwaves; in addition, since the heat is generated by molecular vibration, the reaction heat field distribution is more uniform, the morphology of the product is more uniform, and the carbon material has very high microwave absorption performance and can absorb microwaves quickly and convert the microwaves into heat energy. Therefore, by preparing the carbon material-metal oxide nanomaterial through microwave synthesis, less time is consumed, the yield is higher, and the quality is higher.

According to the preparation method of the present disclosure, preferably, based on the total weight of the carbon material and the metal oxides, the amount of the carbon material is 0.5~20 wt. %, and the amount of the metal oxides is 80~99.5 wt. %; more preferably, based on the total weight of the carbon material and the metal oxides, the amount of the carbon material is 0.5~15 wt. %, and the amount of the metal oxides is 85~99.5 wt. %.

According to the preparation method of the present disclosure, preferably, based on the total weight of the carbon material and the metal oxide precursors measured in the metal oxides, the amount of the carbon material is 0.5~20 wt. %, and the amount of the metal oxide precursors measured in the metal oxides is 80~99.5 wt. %; more preferably, based on the total weight of the carbon material and the metal oxide precursors measured in the metal oxides, the amount of the carbon material is 0.5~15 wt. %, and the amount of the metal oxide precursors measured in the metal oxides is 85~99.5 wt. %.

According to the preparation method of the present disclosure, the carbon material may be any carbon material commonly used in the art; preferably, the carbon material is one or more of graphene, carbon nanotubes, fullerene and carbon black.

In addition, through in-depth research, the inventor has also found that the gas sensing performance can be further improved if the metal oxides contain $WO_3$ and one or more selected from $SnO_2$, $Fe_2O_3$, $TiO_2$, CuO, $MoO_3$ and ZnO. More preferably, the metal oxides contain $WO_3$ and one or more selected from $SnO_2$, $Fe_2O_3$, $TiO_2$, CuO and $MoO_3$.

According to the present disclosure, the alcohol-soluble salts may be various salts that can form the metal oxides after the heat treatment and can be dissolved in an alcohol solvent, or can be dissolved in an alcohol solvent in the presence of a solubilizer. In addition, in the case that a solubilizer is used, preferably the solubilizer is a solubilizer that can be removed in the heat treatment process, thus there is no adverse effect to the preparation of the catalyst and the performance of the product even when the solubilizer is used.

According to the present disclosure, for example, the alcohol-soluble tungsten salt may be one or more of tungsten chloride, tungsten iodide and hexacarbonyl tungsten.

According to the present disclosure, for example, the alcohol-soluble tin salt may be one or more of tin chloride, tin bromide and tin iodide.

According to the present disclosure, for example, the alcohol-soluble iron salt may be one or more of iron chloride, iron bromide, iron nitrate and carbonyl iron.

According to the present disclosure, for example, the alcohol-soluble titanium salt may be one or more of titanium chloride, titanium bromide and titanium iodide.

According to the present disclosure, for example, the alcohol-soluble copper salt may be one or more of copper chloride, copper bromide and copper nitrate.

According to the present disclosure, for example, the alcohol-soluble molybdenum salt may be one or more of molybdenum chloride, molybdenum bromide and molybdenum iodide.

According to the present disclosure, for example, the alcohol-soluble zinc salt may be one or more of zinc chloride, zinc iodide, zinc bromide and zinc nitrate.

According to the present disclosure, to further improve the gas sensing performance, preferably, based on the total weight of the metal oxides, the content of the tungsten oxide preferably is 60~99.5 wt. %, more preferably is 70~99.5 wt. %. Furthermore, measured in the metal oxides, the amount of the alcohol-soluble tungsten salt in the metal oxide precursors is 60~99.5 wt. %, more preferably is 70~99.5 wt. %.

According to the preparation method of the present disclosure, the alcohol solvent may be one or more of ethanol, ethylene glycol and glycerin, for example. Preferably, the alcohol solvent is ethanol.

According to the preparation method of the present disclosure, preferably, in relation to the total weight of the carbon material, and the metal oxides and the metal oxide precursors, which is measured as 100 pbw, the amount of the solvent is 500~100,000 pbw.

Preferably, the conditions of the heat treatment include: microwave power: 200~1,800 W; heat treatment temperature: 160~220° C.; and heat treatment time: 10~240 min.; more preferably, microwave power: 200~1,200 W; heat treatment temperature: 180~220° C.; and heat treatment time: 30~150 min.; further preferably, microwave power: 300~1,000 W; heat treatment temperature: 180~190° C.; and heat treatment time: 40~140 min.

According to the preparation method of the present disclosure, solid-liquid separation is carried out after the heat treatment, and the solid-liquid separation method may be any method usually used for separating solid and liquid in the art, such as centrifugation or filtration.

According to the preparation method of the present disclosure, preferably, the method further comprises a step of washing and drying the carbon material-metal oxide composite nanomaterial obtained through separation. The washing preferably is carried out with the solvent used in the heat treatment, for example, ethanol. The drying may be carried out at 60~100° C. for 2~10 hours, for example.

According to the preparation method of the present disclosure, preferably, the method further comprises a step of reducing the carbon material-metal oxide composite nanomaterial with a reducing agent; or the method further comprises a step of thermally reducing the carbon material-metal oxide composite nanomaterial. Through the reduction step, the power consumption can be further reduced and the sensitivity can be improved.

When the carbon material-metal oxide composite nanomaterial is reduced with a reductant, preferably, a mass ratio of the carbon material-metal oxide composite nanomaterial measured in carbon element to the reductant is 1:(0.1~20), more preferably is 1:(0.1-~10).

Preferably, the reductant is one or more of sodium borohydride, lithium aluminum hydride, hydrogen iodide, hydrogen bromide, thiourea, ethanethiol, sodium persulfate, hydrazine hydrate, pyrrole, urea, ethanol, ascorbic acid, glucose, aluminum-hydrochloric acid, iron-hydrochloric acid, zinc-sodium hydroxide, zinc-ammonium hydroxide, glycine, lysine and green tea.

Preferably, the conditions of the reduction treatment include: reduction treatment temperature: 200~500° C.; and reduction treatment time: 0.1~12 h.

When the carbon material-metal oxide composite nanomaterial is reduced at a high temperature, the temperature may be 200~1,000° C. The higher the temperature is, the higher the degree of reduction is. However, if the temperature is higher than the melting points of the metal oxides, the morphology will change and the gas sensing performance may be affected. If the heating temperature is higher than 1,000° C., a carbothermic reaction will happen between the metal oxide and the carbon material, thus affecting the composition of the product. If the temperature is lower than 200° C., the degree of reduction will be too low, and the resistance will still be high.

According to a third aspect of the present disclosure, the present disclosure provides a self-heating gas sensor based on Joule principle, comprising a chip carrier and a gas-sensitive material supported on the chip carrier, wherein the gas-sensitive material is the gas-sensitive material for a self-heating gas sensor based on Joule principle in the present disclosure.

Preferably, the chip carrier is a ceramic tube and/or a MEMS chip.

The MEMS chip may be, for example, the chip shown in FIG. 1, which comprises a silicon substrate 3 and metal interdigital electrodes 2 formed on the silicon substrate 3, wherein the metal interdigital electrodes 2 are used for current transmission; the silicon substrate 3 provides support for the entire MEMS chip, and has functions of electrical insulation and heat insulation as well.

Preferably, the gas-sensitive material is supported on the chip carrier by dripping, gas spraying, micro-spraying, deposition, or coating.

Before the gas-sensitive material is coated with a coating method, it can be dispersed in an appropriate organic solvent (e.g., ethanol, acetone, glycerol, or terpineol, etc.), and then be ground in an agate mortar, so that the gas-sensitive material is dispersed uniformly in the organic solvent. The mass ratio of the organic solvent to the gas-sensitive material may be (0.1~10): 1, preferably is 1:1. If the organic solvent is excessive, the gas-sensitive material dispersion liquid will be too thin to be coated on the substrate. If the amount of the organic solvent is too small, the gas-sensitive material dispersion liquid will be too thick, resulting in unevenly distributed coating on the substrate and compromised gas sensing performance. Different kinds of organic solvents have different boiling points. Preferably the boiling point is 80~250° C. If the boiling point is too low, the organic solvent will volatilize too quickly in the drying process, which may lead to cracks. If the boiling point is too high, the organic solvent will volatilize too slowly; consequently, it will be difficult to remove the organic solvent.

According to a fourth aspect of the present disclosure, the present disclosure provides a use of the gas-sensitive material provided by the present disclosure in self-heating gas sensors based on Joule principle.

Hereunder the present disclosure will be detailed in some embodiments, but the present disclosure is not limited to the following embodiments.

Example 1

Figure 2:
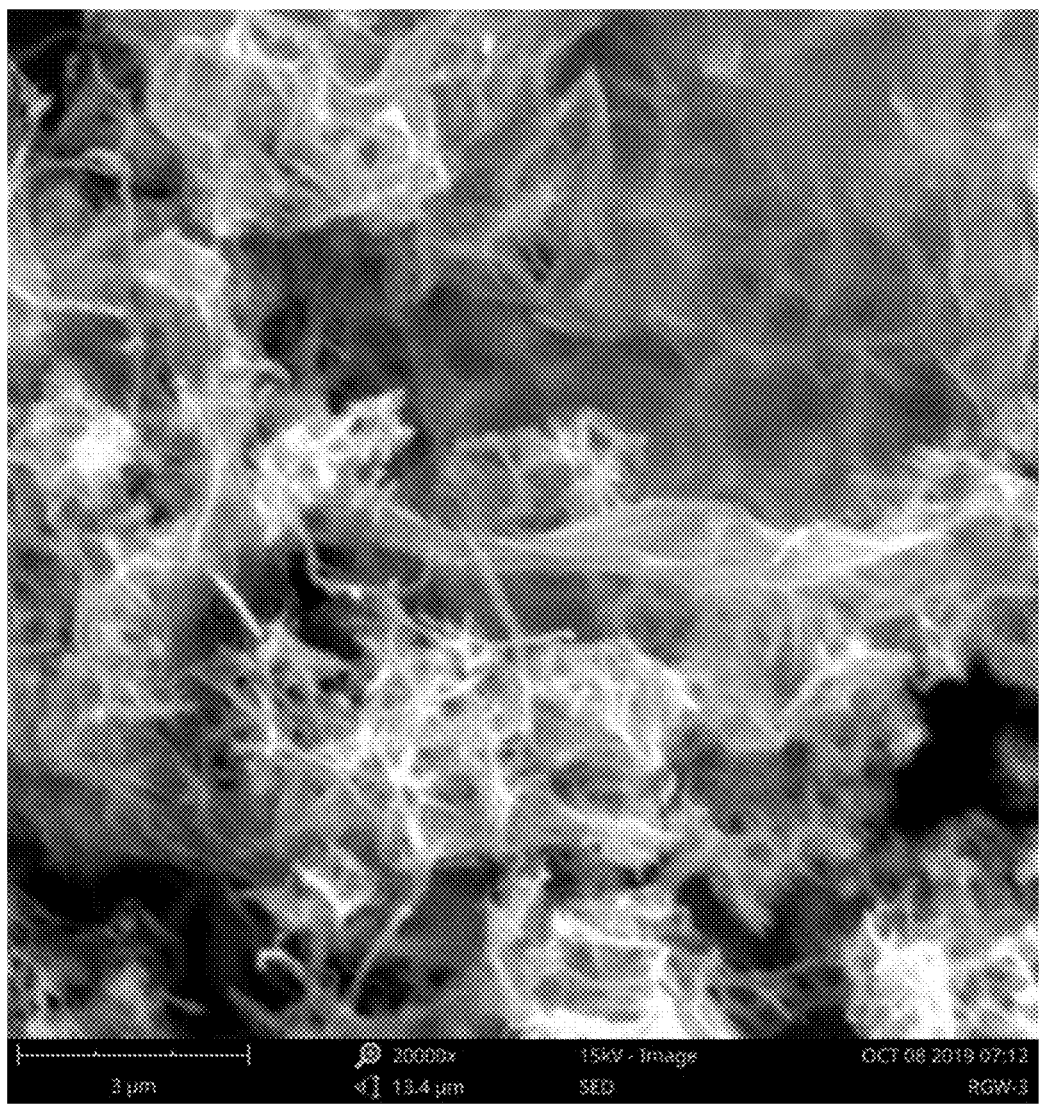
FIG. 2 is a SEM image of the flaky nanomaterial obtained in Example 1.
Figure 3:
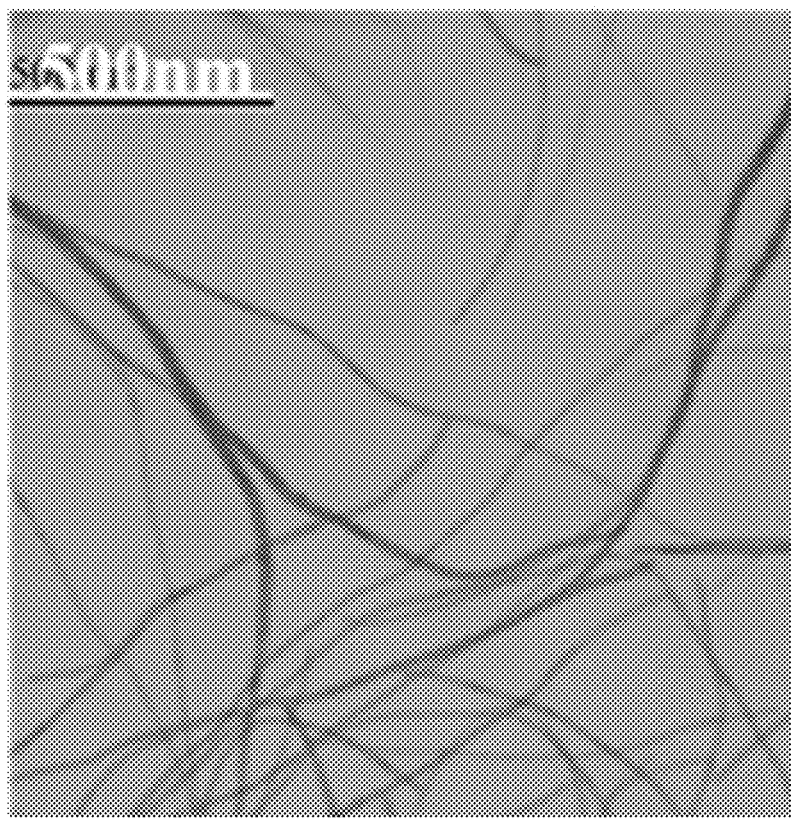
FIG. 3 is a TEM image of the nanowires formed by the flaky nanomaterial on the surface of the carbon material obtained in Example 1.

15 mg graphene oxide, 0.80 g tungsten chloride and 0.20 g $SnCl_4$ were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon material-metal oxide composite nanomaterial A1 (a flaky nanomaterial, the thickness was 1~2 nm, and the longest linear distance between two points was 1~5 μm), wherein the content of the carbon material was 2.5 wt. %, the content of the metal oxide was 97.5 wt. %, and the resistance was 30 kΩ; based on the total weight of the metal oxides, the content of the tungsten trioxide was 80 wt. % and the content of the tin oxide was 20 wt. %. FIG. 2 is a SEM image of the flaky nanomaterial obtained in Example 1. FIG. 3 is a TEM image of the nanowires formed by the flaky nanomaterial on the surface of the carbon material obtained in Example 1. As shown in FIGS. 2 and 3, the flaky nanomaterial has a structure in which nanowires are formed on the surface of the carbon material, and the nanowires have 20~30 nm diameter and 600~4,000 nm length.

In addition, through an XPS test, it is determined that the nanowires contain oxygen, tungsten and tin elements; according to the peak positions in the XPS spectrogram, the valence states of tungsten and tin elements are +6 and +4 respectively; through an XRD test, the peak positions of the above nanowires are compared with tungsten trioxide and tin dioxide in a PDF card. The result demonstrates that all of the peaks can be attributed to the crystal structure of $WO_3$ (JCPDs: 83-0950), and no diffraction peak of Sn oxide is detected, which indicates that Sn does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of $SnO_2$, which indicates that the nanowires are tungsten trioxide doped nanowires formed by doping tin dioxide in tungsten trioxide nanowires.

Example 2

15 mg carbon nanotubes, 0.80 g tungsten chloride and 0.20 g $SnCl_4$ were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon material-metal oxide composite nanomaterial A2 (a linear nanomaterial, the diameter was 5~15 nm, and the length was 10~30 μm), wherein the content of the carbon material is 2.5 wt. %, the content of the metal oxide is 97.5 wt. %, and the resistance is 56 kΩ; based on the total weight of the metal oxides, the content of the tungsten trioxide is 80 wt. % and the content of the tin oxide is 20 wt. %.

In addition, it is seen from the SEM image and TEM image of the linear nanomaterial obtained in Example 2, in the structure of the linear nanomaterial, nanowires are formed on the surface of the carbon material, the diameter of the nanowires is 20~30 nm, and the length of the nanowires is 600~4,000 nm.

In addition, through an XPS test, it is determined that the nanowires contain oxygen, tungsten and tin elements; according to the peak positions in the XPS spectrogram, the valence states of tungsten and tin elements are +6 and +4 respectively; through an XRD test, the peak positions of the above nanowires are compared with tungsten trioxide and tin dioxide in a PDF card. The result demonstrates that all of the peaks can be attributed to the crystal structure of $WO_3$ (JCPDs: 83-0950), and no diffraction peak of Sn oxide is detected, which indicates that Sn does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of $SnO_2$, which indicates that the nanowires are tungsten trioxide doped nanowires formed by doping tin dioxide in tungsten trioxide nanowires.

Example 3

15 mg graphene oxide, 0.8 g tungsten chloride and 0.2 g iron chloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and a small amount of anhydrous ethanol for 3 times. Then the centrifuged sample was loaded into an oven and dried at 80° C. for 6 hours to obtain a carbon material-metal oxide composite nanomaterial A4 (a flaky nanomaterial, the thickness was 1~2 nm, and the longest linear distance between two points was 1~5 μm), wherein the content of the carbon material is 2.5 wt. %, the content of the metal oxide is 97.5 wt. %, and the resistance is 33 kΩ; based on the total weight of the metal oxides, the content of the tungsten trioxide is 70 wt. % and the content of the ferric oxide is 30 wt. %.

Figure 4:
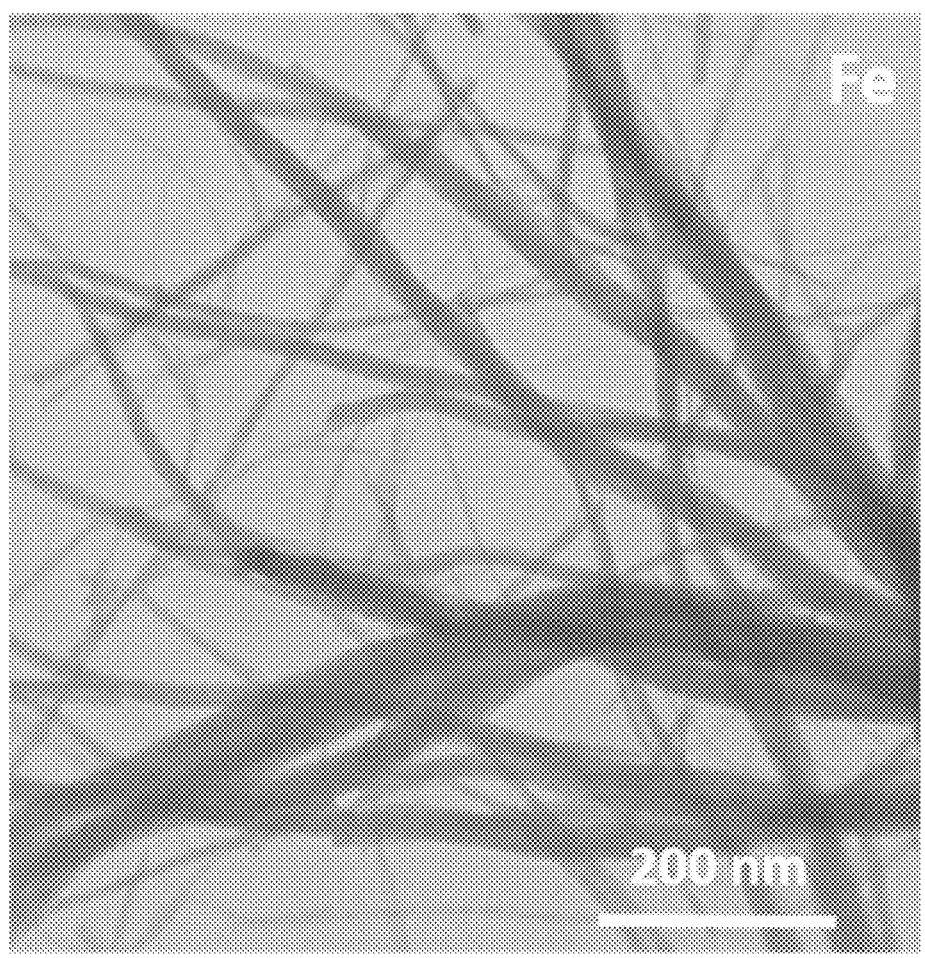
FIG. 4 is a TEM image of the nanowires formed by the flaky nanomaterial on the surface of the carbon material obtained in Example 3.

FIG. 4 is a TEM image of the nanowires formed by the flaky nanomaterial on the surface of the carbon material obtained in Example 3. It is seen from the SEM image and TEM image of the linear nanomaterial obtained in Example 3, in the structure of the flaky nanomaterial, nanowires are formed on the surface of the carbon material, the diameter of the nanowires is 20~30 nm, and the length of the nanowires is 600~4,000 nm.

In addition, through an XPS test, it is determined that the nanowires contain oxygen, tungsten and iron elements; according to the peak positions in the XPS spectrogram, the valence states of tungsten and iron elements are +6 and +3 respectively; through an XRD test, the peak positions of the above nanowires are compared with tungsten trioxide and ferric oxide in a PDF card. The result demonstrates that all of the peaks can be attributed to the crystal structure of $WO_3$ (JCPDs: 83-0950), and no diffraction peak of Fe oxide is detected, which indicates that Fe does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of $Fe_2O_3$, which indicates that the nanowires are tungsten trioxide doped nanowires formed by doping ferric oxide in tungsten trioxide nanowires.

Example 4

Figure 5:
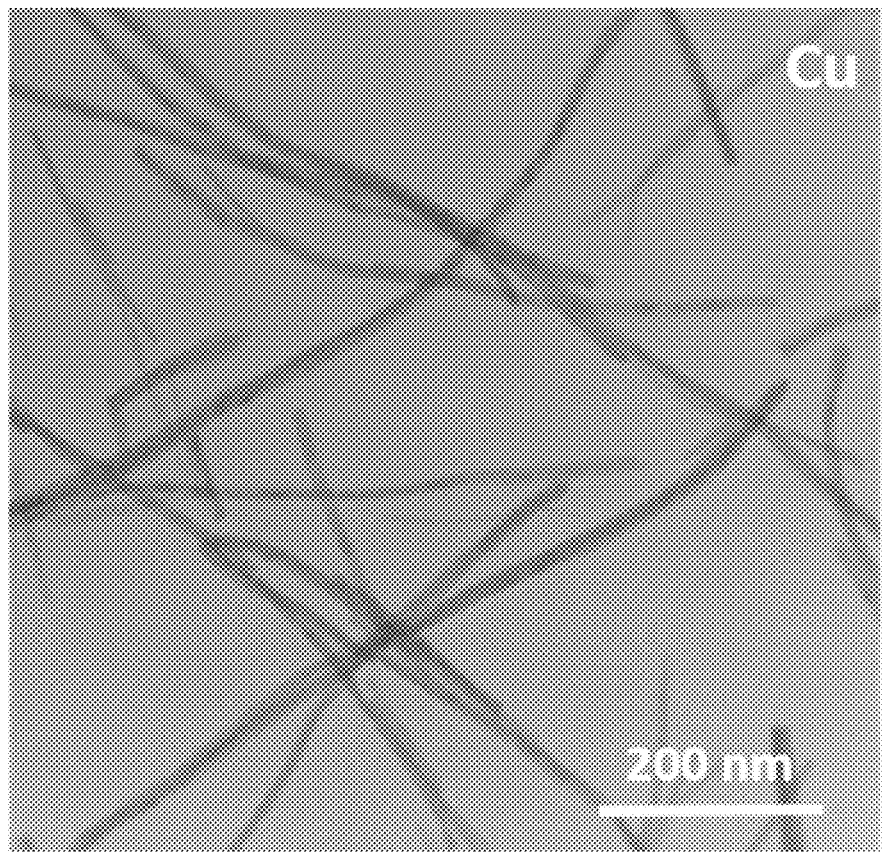
FIG. 5 is a TEM image of the nanowires formed by the flaky nanomaterial on the surface of the carbon material obtained in Example 4.

15 mg graphene oxide, 0.8 g tungsten chloride and 0.2 g copper chloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon material-metal oxide composite nanomaterial A5 (a flaky nanomaterial, the thickness was 1~2 nm, and the longest linear distance between two points was 1~5 μm), wherein the content of the carbon material is 2.5 wt. %, the content of the metal oxide is 97.5 wt. %, and the resistance is 61 kΩ; based on the total weight of the metal oxides, the content of the tungsten trioxide is 80 wt. % and the content of the copper oxide is 20 wt. %. FIG. 5 is a TEM image of the nanowires formed by the flaky nanomaterial on the surface of the carbon material obtained in Example 4. It is seen from the SEM image and TEM image of the linear nanomaterial obtained in Example 4, in the structure of the flaky nanomaterial, nanowires are formed on the surface of the carbon material, the diameter of the nanowires is 20~30 nm, and the length of the nanowires is 600~4,000 nm.

In addition, through an XPS test, it is determined that the nanowires contain oxygen, tungsten and copper elements; according to the peak positions in the XPS spectrogram, the valence states of tungsten and copper elements are +6 and +2 respectively; through an XRD test, the peak positions of the above nanowires are compared with tungsten trioxide and copper oxide in a PDF card. The result demonstrates that all of the peaks can be attributed to the crystal structure of $WO_3$ (JCPDs: 83-0950), and no diffraction peak of Cu oxide is detected, which indicates that Cu does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of CuO, which indicates that the nanowires are tungsten trioxide doped nanowires formed by doping copper oxide in tungsten trioxide nanowires.

Example 5

15 mg graphene oxide, 0.8 g tungsten chloride and 0.2 g titanium tetrachloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon material-metal oxide composite nanomaterial A6 (a flaky nanomaterial, the thickness was 1~2 nm, and the longest linear distance between two points was 1~5 μm), wherein the content of the carbon material is 2.5 wt. %, the content of the metal oxide is 97.5 wt. %, and the resistance is 55 kΩ; based on the total weight of the metal oxides, the content of the tungsten trioxide is 84.7 wt. % and the content of the titanium dioxide is 15.3 wt. %.

Figure 6:
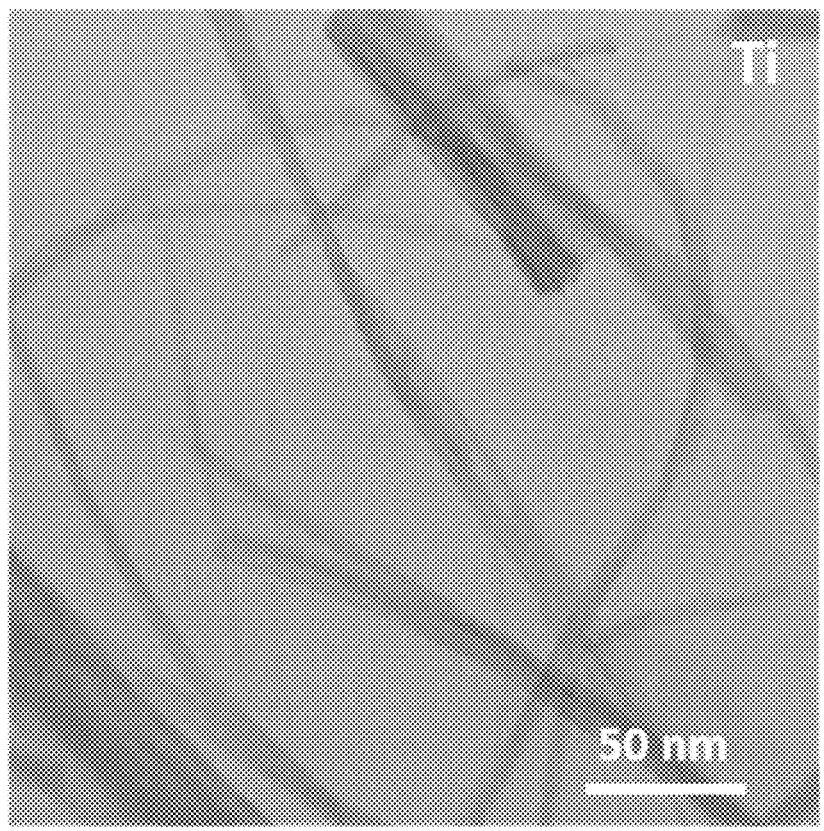
FIG. 6 is a TEM image of the nanowires formed by the flaky nanomaterial on the surface of the carbon material obtained in Example 5.

FIG. 6 is a TEM image of the nanowires formed by the flaky nanomaterial on the surface of the carbon material obtained in Example 5. It is seen from the SEM image and TEM image of the linear nanomaterial obtained in Example 5, in the structure of the flaky nanomaterial, nanowires are formed on the surface of the carbon material, the diameter of the nanowires is 20~30 nm, and the length of the nanowires is 600~4,000 nm.

In addition, through an XPS test, it is determined that the nanowires contain oxygen, tungsten and titanium elements; according to the peak positions in the XPS spectrogram, the valence states of tungsten and titanium elements are +6 and +4 respectively; through an XRD test, the peak positions of the above nanowires are compared with tungsten trioxide and titanium dioxide in a PDF card. The result demonstrates that all of the peaks can be attributed to the crystal structure of $WO_3$ (JCPDs: 83-0950), and no diffraction peak of Ti oxide is detected, which indicates that Ti does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of $TiO_2$, which indicates that the nanowires are tungsten trioxide doped nanowires formed by doping titanium dioxide in tungsten trioxide nanowires.

Example 6

15 mg graphene oxide, 0.8 g tungsten chloride and 0.2 g molybdenum chloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon material-metal oxide composite nanomaterial A7 (a flaky nanomaterial, the thickness was 1~2 nm, and the longest linear distance between two points was 1~5 μm), wherein the content of the carbon material is 2.5 wt. %, the content of the metal oxide is 97.5 wt. %, and the resistance is 50 kΩ; based on the total weight of the metal oxides, the content of the tungsten trioxide is 81.6 wt. % and the content of the molybdenum trioxide is 18.4 wt. %.

It is seen from the SEM image and TEM image of the linear nanomaterial obtained in Example 6, in the structure of the flaky nanomaterial, nanowires are formed on the surface of the carbon material, the diameter of the nanowires is 20~30 nm, and the length of the nanowires is 600~4,000 nm.

In addition, through an XPS test, it is determined that the nanowires contain oxygen, tungsten and molybdenum elements; according to the peak positions in the XPS spectrogram, the valence states of tungsten and molybdenum elements are +6 and +6 respectively; through an XRD test, the peak positions of the above nanowires are compared with tungsten trioxide and molybdenum trioxide in a PDF card. The result demonstrates that all of the peaks can be attributed to the crystal structure of $WO_3$ (JCPDs: 83-0950), and no diffraction peak of Mo oxide is detected, which indicates that Mo does not form a separate crystal phase, but is embedded in the lattice of $WO_3$ in the form of ions; through a HRTEM test, it is observed that the lattice spacing of the doped nanowires is 0.387 nm, which corresponds to the crystal plane (001) of $WO_3$; and there is no corresponding crystal plane of $MoO_3$, which indicates that the nanowires are tungsten trioxide doped nanowires formed by doping molybdenum trioxide in tungsten trioxide nanowires.

Example 7

A carbon material-metal oxide composite nanomaterial A1 was prepared with the method in Example 1, then 100 mg carbon material-metal oxide composite nanomaterial A1 was weighed accurately and the sample was added into a 50 mL beaker, 200 μL hydrazine hydrate was added dropwise, the beaker was sealed with a plastic wrap, placed in water bath, and kept at 90° C. constant temperature for 5 hours;

thus a carbon material-metal oxide composite nanomaterial A8 in which the degree of reduction of graphene was improved was obtained.

Comparative Example 1

The preparation was carried out with the method in Example 1, but the tungsten chloride and SnCl$_4$ were replaced with tungsten chloride, and a reduced graphene WO$_3$ nanomaterial D1 was obtained, wherein the content of the carbon material was 0.4 wt. %, the content of the metal oxides was 99.6 wt. %, and the resistance was 120 kΩ.

Comparative Example 2

The preparation was carried out with the method in Example 1, but the tungsten chloride and SnCl$_4$ were replaced with tungsten chloride, and a reduced graphene WO$_3$ nanomaterial D2 was obtained, wherein the content of the carbon material was 25 wt. %, the content of the metal oxides was 75 wt. %, and the resistance was 500 kΩ.

Comparative Example 3

15 mg graphene oxide and 1 g tungsten chloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a reduced graphene WO$_3$ nanomaterial D3 (a flaky nanomaterial, the thickness was 1~2 nm, and the longest linear distance between two points was 1~5 μm), wherein the content of the carbon material was 2.5 wt. %, the content of the metal oxides was 97.5 wt. %, and the resistance was 40 kΩ.

Comparative Example 4

15 mg carbon nanotubes and 1 g tungsten chloride were weighed accurately and added into a 500 mL beaker, then 300 mL anhydrous ethanol was poured into the beaker, the mixture was stirred for about 30 minutes by magnetic stirring, and then was ultrasonically crushed for 30 minutes with a cell breaker; then, the obtained mixed solution was poured into 10 50 mL polytetrafluoroethylene reactors, heated up to 200° C. with a microwave synthesizer with 800 W power, and then kept at the temperature for 2 hours. After the reaction, the product was centrifuged and washed with deionized water and anhydrous ethanol for 3 times. Then the centrifuged sample was loaded into an oven and dried at 80° C. for 6 hours to obtain a carbon nanotubes WO$_3$ nanomaterial D4 (a linear nanomaterial, the diameter was 5~15 nm, and the length was 10~30 μm), wherein the content of the carbon material was 2.5 wt. %, the content of the metal oxides was 97.5 wt. %, and the resistance was 60 kΩ.

Comparative Example 5

The preparation was carried out with the method in Example 3, but the tungsten chloride was replaced with copper chloride; thus, a reduced graphene copper oxide nanomaterial D6 (a flaky nanomaterial, the thickness was 1~2 nm, the longest linear distance between two points was 1~5 μm) was obtained, wherein the content of the carbon material was 2.5 wt. %, the content of the metal oxides was 97.5 wt. %, and the resistance was 70 kΩ.

Comparative Example 6

The preparation was carried out with the method in Example 3, but the tungsten chloride was replaced with molybdenum chloride; thus, a reduced graphene molybdenum oxide nanomaterial D7 (a flaky nanomaterial, the thickness was 1~2 nm, the longest linear distance between two points was 1~5 μm) was obtained, wherein the content of the carbon material was 2.5 wt. %, the content of the metal oxides was 97.5 wt. %, and the resistance was 80 kΩ.

Comparative Example 7

Commercially purchasing: planar multilayer electrodes purchased from Beijing Elite Technology Co., Ltd.

Comparative Example 8

The preparation was carried out with the method in Example 1, but the anhydrous ethanol was replaced with deionized water in the microwave synthesis; thus, a carbon material-metal oxide composite nanomaterial D8 was obtained.

Figure 7:
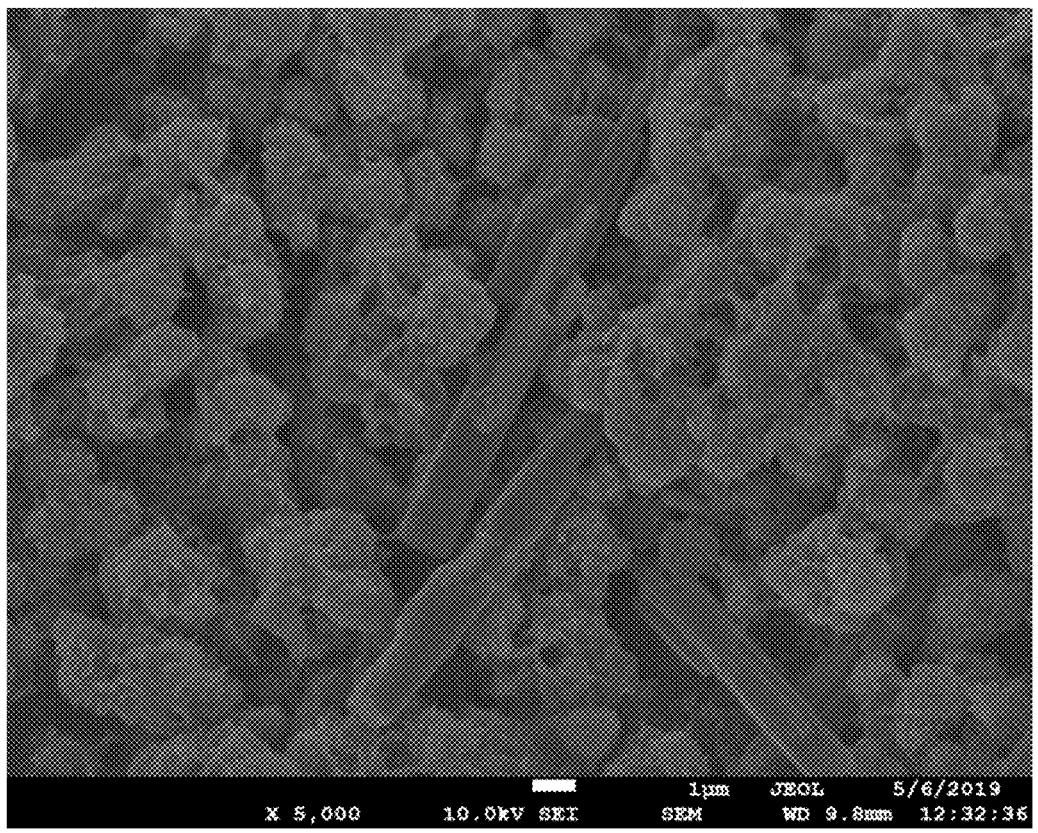
FIG. 7 is a SEM image of the nanomaterial obtained in Comparative Example 8.

FIG. 7 is a SEM image of the nanomaterial obtained in Comparative Example 8. It is seen from FIG. 7 that rod-shaped and sphere-shaped nano-WO$_3$ structures are obtained after ethanol is replaced with water.

Comparative Example 9

The preparation was carried out with the method in Example 1, but a surfactant urea was added in the microwave synthesis; thus, a carbon material-metal oxide composite nanomaterial D9 was obtained.

It is seen from the SEM image that irregular semi-tubular nano-WO$_3$ structures were obtained.

Test Example 1

Gas sensors were prepared with the nanomaterials A1-A7 obtained in Examples 1~7 and the materials D1~D6 obtained in Comparative Examples 1~6 respectively. The preparation method is as follows: 100 mg nanomaterial was weighed accurately and added into an agate mortar, 100 μL terpineol was added into the agate mortar, and the mixture was ground for 10 minutes; the ground slurry was coated uniformly with a writing brush on the metal interdigital electrodes 2 of a MEMS chip to form a gas-sensitive material layer 1, then the MEMS chip was heated up to 80° C. in an oven and kept at the temperature for 12 hours. The MEMS chip was connected to a test base by means of a wire bonding machine, and the base was inserted into an aging tester and aged for 7 days at 400° C.; thus, gas sensors B1~B7 and DB1~DB6 were obtained. In addition, planar multi-layer electrodes purchased from Beijing Elite Technology Co., Ltd. were used as DB7.

As shown in FIG. 1, a power source meter 4 and an ohmmeter 5 were connected to the gas sensors respectively, and the power source meter was used to provide a voltage to heat up the gas sensors B1~B9 and DB1~DB8 from 25° C.

respectively; thus, power values under different temperature conditions were obtained. The result is shown in Table 1.

TABLE 1

|     | Power consumed to heat up to 50° C. (µW) | Power consumed to heat up to 100° C. (µW) | Power consumed to heat up to 200° C. (µW) |
|-----|------|-------|--------|
| B1  | 69   | 866   | 4792   |
| B2  | 102  | 1276  | 7056   |
| B3  | 72   | 915   | 5322   |
| B4  | 80   | 998   | 5321   |
| B5  | 76   | 965   | 5133   |
| B6  | 73   | 894   | 4922   |
| B7  | 62   | 760   | 4630   |
| DB1 | 253  | 3220  | 17350  |
| DB2 | 792  | 10112 | 60230  |
| DB3 | 82   | 1020  | 5930   |
| DB4 | 112  | 1533  | 8245   |
| DB5 | 144  | 1822  | 10383  |
| DB6 | 165  | 2331  | 11857  |
| DB7 | 10030| 34203 | 105203 |

Test Example 2

The gas sensors B1~B7 and DB1~DB9 were put into a sealed chamber respectively and connected with a power source meter and an ohmmeter respectively, the voltage and current were logged, and the resistance $R_0$ of each sensor was obtained under the Ohm's Law; then 10 ppm hydrogen sulfide gas was introduced into the sealed chamber, so that the resistance of the gas sensor was decreased; after the resistance was stabilized, the sensor resistance $R_1$ and the response value of the gas sensor $S=(R_0-R_1)/R_0*100\%$ were logged, the response time $t_1$ was determined as the time when the resistance was decreased by 900%; then the hydrogen sulfide gas was stopped and air was introduced into the chamber, so that the sensor resistance began to recover, the recovery time $t_2$ was determined as the time when the resistance was recovered by 90%. The response value in the entire process was plotted against time, and the response value and response recovery time of each gas sensor to hydrogen sulfide at 5V voltage were obtained. The result is shown in Table 2.

TABLE 2

|     | Response Value (at 200° C.) | Response Recovery Time |
|-----|------|--------|
| B1  | 65   | <20 s  |
| B2  | 63   | <20 s  |
| B3  | 59   | <20 s  |
| B4  | 58   | <20 s  |
| B5  | 57   | <20 s  |
| B6  | 56   | <20 s  |
| B7  | 63   | <20 s  |
| DB1 | 50   | <30 s  |
| DB2 | 28   | <180 s |
| DB3 | 51   | <30 s  |
| DB4 | 48   | <30 s  |
| DB5 | 46   | <30 s  |
| DB6 | 43   | <30 s  |
| DB7 | 33   | <30 s  |
| DB8 | 27   | <30 s  |
| DB9 | 18   | <30 s  |

While the present disclosure is described above in detail in some preferred embodiments, the present disclosure is not limited to those embodiments. Various simple variations, including combinations of the technical features in any other appropriate way, can be made to the technical scheme of the present disclosure within the scope of the technical concept of the present disclosure, but such variations and combinations shall be deemed as disclosed content in the present disclosure and falling in the protection scope of the present disclosure.

The invention claimed is:

1. A gas-sensitive material, comprising 0.5-20 wt. % of a carbon material and 80-99.5 wt. % of metal oxides,
   wherein the metal oxides comprises tungsten oxide and a dopant selected from tin oxide, iron oxide, titanium oxide, copper oxide, molybdenum oxide, zinc oxide, and mixtures thereof, and
   wherein the tungsten oxide forms a plurality of nanowires on the carbon material, and the plurality of nanowires comprises tungsten oxide crystals doped with the dopant.

2. A gas sensor comprising a chip carrier and the gas-sensitive material of claim 1 supported on the chip carrier.

3. The gas sensor of claim 2, wherein the gas-sensitive material is deposited on the chip carrier by dripping, gas spraying, micro-spraying, deposition, or coating.

4. The self-heating gas sensor of claim 2, wherein the chip carrier is a ceramic tube and/or a chip comprising a silicon substrate and metal interdigital electrodes formed on the silicon substrate.

5. The gas-sensitive material of claim 1, wherein each of the plurality of nanowires has a diameter of 10-100 nm, and a length of 500-10,000 nm.

6. The gas-sensitive material of claim 1, wherein the tungsten oxide is $WO_3$ and the dopant is selected from $SnO_2$, $Fe_2O_3$, $TiO_2$, $CuO$, $MoO_3$, $ZnO$, and mixtures thereof.

7. The gas-sensitive material of claim 6, wherein based on the total weight of the metal oxides, the content of the tungsten oxide is 60-99.5 wt. %.

8. The gas-sensitive material of claim 6, wherein the nanowires are tungsten trioxide-doped nanowires.

9. The gas-sensitive material of claim 1, comprising 0.5-15 wt. % of the carbon material and 85-99.5 wt. % of the metal oxides.

10. The gas-sensitive material of claim 1, wherein the carbon material is one or more selected from graphene, carbon nanotubes, fullerene, and carbon black.

11. A method for preparing a gas-sensitive material, comprising the steps of carrying out heat treatment on a carbon material, and metal oxides and/or metal oxide precursors under microwaves in the presence of an alcohol solvent, and then carrying out solid-liquid separation, to obtain a carbon material-metal oxide composite nanomaterial,
   wherein the metal oxides contain tungsten oxide and one or more selected from tin oxide, iron oxide, titanium oxide, copper oxide, molybdenum oxide and zinc oxide;
   the metal oxide precursors are alcohol-soluble tungsten salt and one or more selected from alcohol-soluble tin salt, alcohol-soluble iron salt, alcohol-soluble titanium salt, alcohol-soluble copper salt, alcohol-soluble molybdenum salt and alcohol-soluble zinc salt.

12. The method of claim 11, wherein no surfactant is used in the heat treatment.

13. The method of claim 11, wherein based on the total weight of the carbon material and the metal oxides, the amount of the carbon material is 0.5-20 wt. %, and the amount of the metal oxides is 80-99.5 wt. %; or
   based on the total weight of the carbon material and the metal oxide precursors measured in the metal oxides, the amount of the carbon material is 0.5-20 wt. %, and the amount of the metal oxide precursors measured in the metal oxides is 80-99.5 wt. %.

14. The method of claim 13, wherein the carbon material is one or more selected from graphene, carbon nanotube, fullerene, and carbon black.

15. The method of claim 13, wherein the metal oxides contain $WO_3$ and one or more selected from $SnO_2$, $Fe_2O_3$, $TiO_2$, CuO, $MoO_3$, and ZnO.

16. The method of claim 13, wherein measured in the metal oxides, the amount of the alcohol-soluble tungsten salt in the metal oxide precursors is 60-99.5 wt. %.

17. The method of claim 13, wherein measured in the total weight of the metal oxides, the content of the tungsten oxide is 60-99.5 wt. %.

18. The method of claim 11, wherein the alcohol solvent is ethanol.

19. The method of claim 11, the conditions of the heat treatment include:
  microwave power: 200-1,800 W; heat treatment temperature: 160-220° C.; and heat treatment time: 10-240 min.

20. The method of claim 11, further comprising a step of reducing the carbon material-metal oxide composite nanomaterial with a reductant.

* * * * *